United States Patent [19]

Sturm

[11] Patent Number: 4,733,078
[45] Date of Patent: Mar. 22, 1988

[54] MEASUREMENT OF MOISTURE-STRATIFIED SHEET MATERIAL

[75] Inventor: Steven P. Sturm, Columbus, Ohio

[73] Assignee: AccuRay Corporation, Columbus, Ohio

[21] Appl. No.: 899,611

[22] Filed: Aug. 25, 1986

[51] Int. Cl.⁴ .................... G01J 1/00; G01F 23/00
[52] U.S. Cl. ..................... 250/339; 250/358.1; 250/359.1
[58] Field of Search ............... 250/339, 358.1, 359.1, 250/360.1, 353, 341; 356/429; 350/276 R, 276 SL

[56] References Cited

U.S. PATENT DOCUMENTS

| | | | |
|---|---|---|---|
| 3,405,268 | 10/1968 | Brunton | 250/339 |
| 3,488,103 | 1/1970 | Webb | 350/276 |
| 3,662,170 | 5/1972 | Keyes | 250/83.3 |
| 3,793,524 | 2/1974 | Howarth | 250/339 |
| 3,879,607 | 4/1975 | Bjorklund | 250/252 |
| 4,027,161 | 5/1977 | Williams et al. | 250/339 |
| 4,052,615 | 10/1977 | Cho | 250/341 |
| 4,306,151 | 12/1981 | Chase | 250/341 |
| 4,577,104 | 3/1986 | Sturm | 250/339 |

Primary Examiner—Janice A. Howell
Attorney, Agent, or Firm—Joseph R. Black, Jr.

[57] ABSTRACT

A process and apparatus for measuring moisture content of moisture-stratified sheet material such as paper is disclosed. The effective reflectivities of two areas of an infrared moisture sensor that generally face opposite surfaces of the sheet are made significantly different, so that the sensitivity of the measurement to conditions prevailing in a high-moisture stratum of the sheet is increased.

14 Claims, 5 Drawing Figures

MEASUREMENT OF MOISTURE-STRATIFIED SHEET MATERIAL

TECHNICAL FIELD OF THE INVENTION

This invention relates to processes for measuring and controlling the moisture content of sheet material using infrared means, and to apparatus adapted for use therein. More particularly, the invention relates to such processes and apparatus that produce accurate measurements of moisture content irrespective of whether the distribution of moisture through the thickness dimension of the sheet is uniform or stratified.

DESCRIPTION OF THE BACKGROUND ART

Systems for measuring the moisture content of sheet material (such as paper) during its production are well-known in the art. A class of such systems makes use of the selective absorption of certain wavelengths of infrared radiation by water.

In the typical operation of these systems, infrared radiation is directed toward the sheet from a source within a traversing sensor. The radiation interacts with the sheet via absorption, scattering, or transmission. By suitable optical filtering, unabsorbed radiation of at least two different wavelengths is separately detected by one or more detectors, which in turn produce two or more voltage responses from which a measurement of moisture content is derived. The following patents exemplify systems of the type generally described above: U.S. Pat. Nos. 3,228,282 Barker, and 3,405,268 Brunton.

A number of modifications to the above-described systems have been made to compensate for measurement error resulting from changes in composition of the sheet material, or from variations in scattering power. Thus, U.S. Pat. No. 4,052,615 Cho discloses an apparatus with two hemispherically concave reflecting surfaces having a particular dimension in relation to the pass gap (distance between a source unit and a detector unit) and to the diameter of the source beam in order to compensate for variations in the scattering characteristics of the sheet. U.S. Pat. No. 4,306,151 Chase discloses a method for measuring the moisture content of paper that is contaminated with carbon. U.S. Pat. No. 4,577,104 Sturm discloses apparatus for measuring the moisture content of sheet material having both variable scattering characteristics and a contaminant, via separate measurement of absorption at four different infrared wavelengths.

Other complications in measuring the moisture content of sheet material, such as paper, derive not so much from the presence of contaminants or variations in scattering power as from the relative amounts of usual constituents of the material which are present in a particular application. U.S. Pat. No. 3,793,524 Howarth discloses an apparatus for measuring moisture content in lightweight papers such as tissues, whereby an offset geometry is employed in conjunction with two planar reflecting surfaces to effect multiple interaction of infrared radiation with the sheet material in order to increase the sensitivity of the apparatus to moisture content.

Another complication relates to temporary moisture stratification along the thickness dimension of the sheet. This is commonly caused by various process control operations. For example, it is a common practice in papermaking to alter the moisture content of the paper web at selected cross-machine zones thereof in order to control its moisture profile. This may be accomplished by a variety of methods including the use of spray dampening ("rewetting") systems or heating systems. See, e.g., U.S. Pat. Nos. 4,188,731 Rauskolb and 4,378,639 Walker.

When some of the these operations are performed, particularly that of rewetting, a temporary period of substantial moisture stratification occurs. In an absorbent material such as paper the moisture will eventually equilibrate so that moisture content is substantially uniform throughout the thickness of the sheet. However, if the moisture measurement is made during the period of moisture stratification by an infrared moisture sensor that is calibrated with samples which have uniform moisture content (which, ordinarily, must be the case), the measurement will be lower than the actual moisture content. This is believed to result from a low effective path length for the radiation as it travels through a high-moisture stratum of the sheet. The low effective path length in turn results from the relative scarcity of cellulosic fibers in the high-moisture stratum, and the correspondingly low amount of scattering in that layer.

The above moisture control operations are typically not performed to a consistent degree for a given cross-machine zone of the sheet material. Nor are they typically performed to the same degree in all cross-machine zones. For example, a spray dampening system may rewet the sheet in a particular zone for a given period of time at a given rate of application, and then at a different rate of application during a subsequent period, or it may cease application altogether. Therefore, there is a need for an infrared moisture sensor which will accurately measure the moisture content of sheet material under conditions of either a uniform or a stratified moisture distribution.

It has been discovered that by adjusting the relative, effective reflectivities of two areas of the sensor which generally face opposite surfaces of the sheet material, an accurate measurement can be produced under both of the above-stated conditions.

SUMMARY OF THE INVENTION

This invention provides apparatus and associated processes for measuring the moisture content of sheet material such as paper. The apparatus comprise a source unit and detector unit having first and second areas, respectively, which generally face opposite first and second surfaces of the sheet material. Disposed within the source unit are means for directing infrared radiation onto the first surface of the sheet. Disposed within the detector unit are means for detecting infrared radiation emitted from the directing means and repeatedly interacting with the sheet and with the first and second areas. The effective reflectivity of one of the first and second areas is significantly greater than that of the other area. This difference in effective reflectivity yields greater measurement sensitivity to moisture conditions prevailing in the sheet near the surface thereof that faces the more reflective area than to those conditions prevailing near the surface that faces the less reflective area. The apparatus are designed to enable accurate measurement of moisture content during a period of substantial moisture stratification in the sheet. To compensate for what would otherwise be a low measurement, the more reflective of the first and second areas is positioned on a side of the sheet corresponding to a high-moisture stratum thereof.

The apparatus may incorporate any conventional means, or other means disclosed herein, for adjusting the effective reflectivity of at least one of the first and second areas so that the apparatus can be tuned to provide the correct degree of compensation for an otherwise incorrect moisture measurement.

The shape and configuration of the first and second areas are not of particular importance, provided the overall geometry of the apparatus is designed to cause multiple interaction of the radiation with the sheet and with the first and second areas. However, it is preferred that the first and second areas be either planar or spherically concave so that the invention can be easily incorporated in existing designs.

Typically, the detected radiation will comprise two sets of wavelengths in the infrared region, one set being of about $1.83\mu$ and $1.93\mu$, and the other set being of about $1.89\mu$ and $2.12\mu$.

An object of the invention is to provide a moisture sensor that, when calibrated by conventional methods, will enable accurate measurement of the moisture content of sheet material irrespective of whether the distribution of moisture is uniform or stratified, as indicated along the thickness dimension of the sheet.

DETAILED DESCRIPTION

For purposes of description, and without intention to limit the scope of this invention, the invention is herein described and illustrated as embodied in a sensor design similar to that shown in U.S. Pat. No. 4,052,615 Cho, the disclosure of which is incorporated herein by reference.

Figure 1:
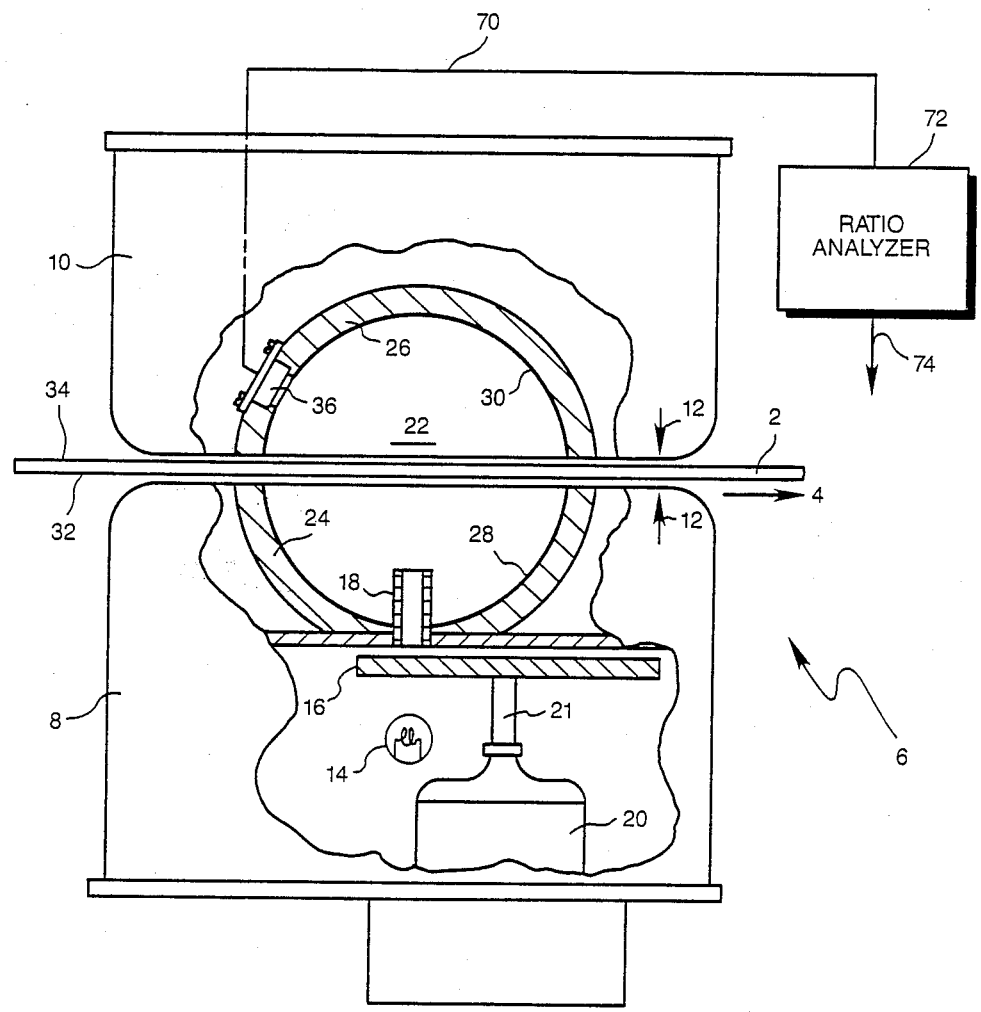
FIG. 1 is a generally schematic, partially sectional view of an embodiment of the invention.

Referring to FIG. 1, the numeral 2 designates a web of sheet material (hereinafter "sheet") that is in motion during production thereof, as indicated at 4. An infrared moisture sensor 6 in accordance with the invention comprises a source unit 8 and a detector unit 10 disposed on opposite sides of the sheet 2 to form a pass gap 12 that is sufficiently wide to enable free movement of the sheet therethrough. The moisture sensor 6 is typically mounted on a conventional sheet-traversing structure (not shown) and moves back and forth across the width of the sheet 2 in a direction that can be viewed as extending into and out from the drawing, thus permitting the sensor to effect measurement in a plurality of cross-machine zones of the sheet.

Disposed within the source unit 8 is a conventional lamp 14 that emits electromagnetic radiation in a spectral band that includes the infrared region. A chopper disc 16 is positioned between the lamp 14 and a light pipe 18, and is driven by a motor 20 through a shaft 21. Separately mounted in the chopper disc 16 are two or more filters (not shown). Typically, four filters are provided which pass infrared radiation wavelengths of about $1.83\mu$, $1.93\mu$, $1.89\mu$, and $2.12\mu$.

A generally spherical cavity 22 is formed by two generally hemispherical bodies 24, 26 mounted in the source unit 8 and detector unit 10, respectively. Hemispherical body 24 has a spherically concave first area 28 which has a first reflectivity. Hemispherical body 26 has a spherically concave second area 30 which has a second reflectivity differing significantly from the first reflectivity. The first area 28 generally faces a first surface 32 of the sheet 2, whereas the second area 30 generally faces a second surface 34 of the sheet.

Disposed within the detector unit 10 is a detector 36. The detector 36 is mounted in the hemispherical body 26 to detect radiation entering the spherical cavity 22. Typically, the active element (not shown) in the detector 36 is located behind a bandpass filter (not shown) that is selected to pass radiation wavelengths that are passed by the filters in the chopper disc 16, but to attenuate a substantial amount of ambient radiation which enters the spherical cavity 22 through the pass gap 12.

As stated above, the reflectivities of the first and second areas 28, 30 are significantly different. The more reflective of the first and second areas 28, 30 will be that area which is positioned on a side of the sheet 2 corresponding to a high-moisture stratum thereof. For example, if the sheet 2 is rewet from the side on which the source unit 8 is disposed, then the first area 28 will be the more reflective. Conversely, if the sheet 2 is rewet from the opposite side, then the second area 30 will be the more reflective. In general, as long as the overall geometry of the sensor 6 is designed to cause radiation reflected from the first and second areas 28, 30 to multiply interact with the first and second surfaces 32, 34 of the sheet 2, the sensor can be adapted to yield greater measurement sensitivity to moisture conditions in the sheet that prevail near the first surface than to those conditions which prevail near the second surface, or vice-versa, depending on which of the first and second areas is the more reflective. Accordingly, when the moisture measurement is made during a period of substantial moisture stratification, the low measurement that would otherwise be observed can be corrected by providing a difference in the effective reflectivities of the first and second areas 28, 30 that is significant enough to compensate for the error caused by stratification.

The phrase "substantial moisture stratification" is herein intended to mean that the equilibration of moisture through the thickness dimension of the sheet 2 is less than 80 percent complete. It is observed that for prior systems, the error caused by stratification of moisture is insignificant when such stratification is not "substantial" as defined.

The "effective reflectivity" of either the first area 28 or second area 30 may be the actual reflectivity of the area, or the reflectivity as "seen" by the sheet 2 when means for adjusting effective reflectivity 38 (FIG. 2) are employed.

The desired difference in effective reflectivity can be expected to vary with the application, and will in general depend on the reflectivity which the sheet 2 has in the "bone-dry" state and, to a small extent, on the basis weight of the sheet. The "bone-dry" reflectivity is affected by contamination of the sheet material. In paper, for example, the use of recycled pulp causes contamination in the form of carbon. Therefore, the desired difference depends on optical effects that are peculiar to the particular sheet material being measured.

These effects can be modeled using the isotropic scattering theories of Kubelka and Munk in order to arrive at nominal reflectivity values for the first and second areas 28, 30. These reflectivity values can then be adjusted for a normally-calibrated sensor so that it accurately indicates moisture content under conditions of either uniform or stratified moisture distribution.

Figure 5:
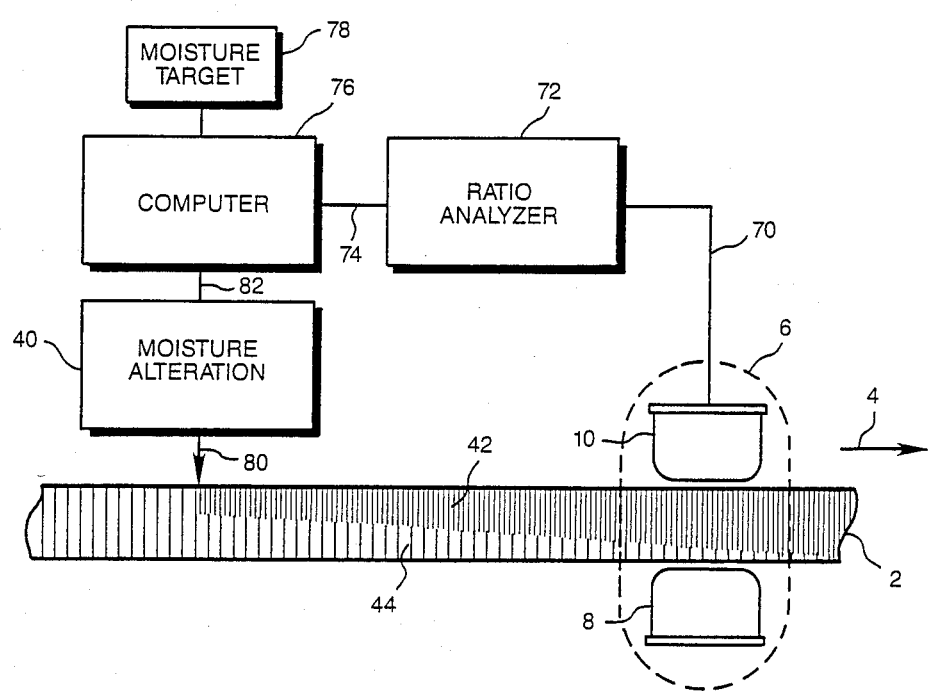
FIG. 5 is a schematic illustration of a process in accordance with the invention.

To facilitate modeling, the sheet 2 is viewed as having two distinct strata as shown in FIG. 5, wherein the strata are designated by the numerals 42 and 44, respectively.

The total transmissivity (T(n)) of the sheet 2 is calculated for each wavelength (n) of interest as follows:

$$T(n) = \frac{(T_{42}(n) \cdot T_{44}(n))}{(1 - R_{42}(n) \cdot R_{44}(n))} \quad (1)$$

where
- $T_{42}(n)$ = transmissivity of stratum 42 for radiation of wavelength n;
- $T_{44}(n)$ = transmissivity of stratum 44 for radiation of wavelength n;
- $R_{42}(n)$ = reflectivity of stratum 42 for radiation of wavelength n; and
- $R_{44}(n)$ = reflectivity of stratum 44 for radiation of wavelength n.

The reflectivity of the combined strata 42 and 44 at wavelength "n" will be different for the two sides of the sheet 2. The reflectivity (RS(n)) on the side where the source unit 8 is located is calculated as follows:

$$RS(n) = R_{42}(n) + \frac{(T_{42}(n)^2 \cdot R_{44}(n))}{(1 - R_{42}(n) \cdot R_{44}(n))} \quad (2)$$

The reflectivity (RD(n)) on the side where the detector unit 10 is located is:

$$RD(n) = R_{44}(n) + \frac{(T_{44}(n)^2 \cdot R_{42}(n))}{(1 - R_{42}(n) \cdot R_{44}(n))} \quad (3)$$

Taking the reflectivity ($R_1$) of the first area 28 into account, the radiation transmitted ($T_d$) and reflected ($R_d$) at wavelength "n" to the detector side is:

$$T_d(n) = \frac{T(n)}{(1 - R_1 \cdot RS(n))} \quad (4)$$

$$R_d(n) = RD(n) + \frac{(T(n)^2 \cdot R_1)}{(1 - R_1 \cdot RD(n))} \quad (5)$$

Taking into account the reflectivity ($R_2$) of the second area 30, but neglecting the transmissivities of the surfaces corresponding to the first and second areas 28, 30, the radiation (I) at wavelength n which is detected at 36 is:

$$I(n) = T_d/(1 - R_2 \cdot R_d(n)) \quad (6)$$

The transmissivities of the surfaces corresponding to the first and second areas 28, 30 act as multipliers in the above equations, thus permitting cancellation of these effects when the ratio of "I" at two different wavelengths is taken.

Modeling is carried out by incrementing and decrementing, as necessary, the weights and moisture levels for each layer to simulate a number of different stratification conditions. The transmissivity and reflectivity of each layer are calculated using Kubelka-Munk scattering equations. Equations 1 through 6 are then used to evaluate the effects of $R_1$ and $R_2$. Optimization is effected by selecting values for $R_1$ and $R_2$ such that the ratio of $I(1.83\mu) / I(1.93\mu)$ is nearly the same for all conditions of stratification.

Since modeling will yield only nominal values for $R_1$ and $R_2$, some adjustment may be needed to ensure that the effective reflectivities of the first and second areas 28, 30 will compensate for the effects of moisture stratification to the correct degree.

In general, if the less reflective of the first and second areas 28, 30 is very reflective, it will be difficult to attain a reflectivity for the more reflective area that is high enough to effect compensation. For this reason, it is preferred to provide a constant reflectivity for one of the two areas, and to provide means for adjusting the effective reflectivity of the other area.

Figure 2:
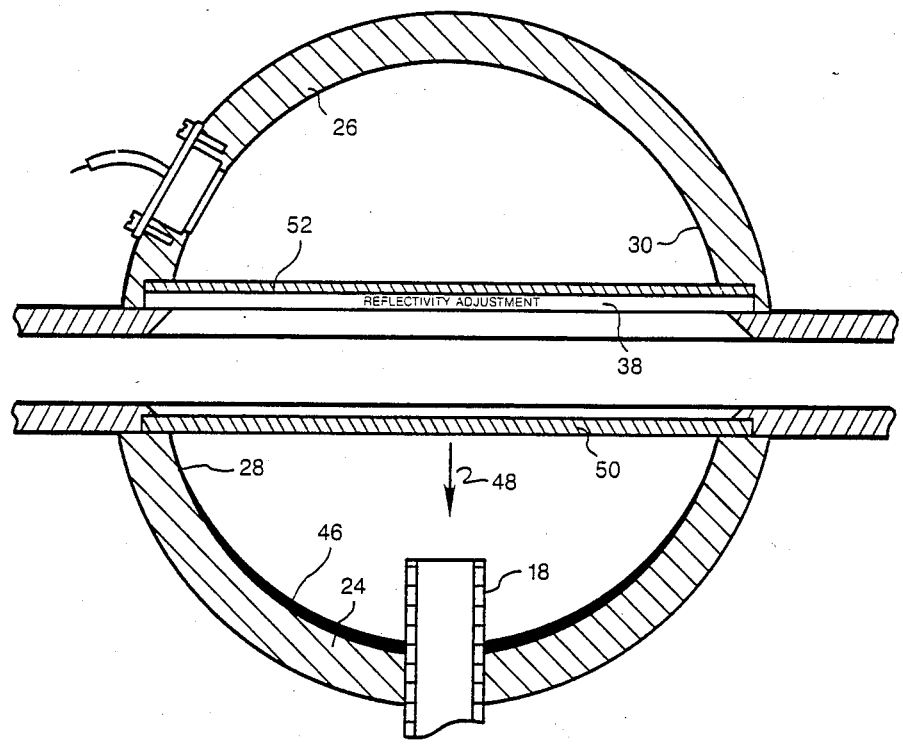
FIG. 2 is a generally schematic, partially sectional view of another embodiment of the invention.

Referring to FIG. 2, the normally mirrorlike surface corresponding to the first area 28 may have a low-reflectivity region 46 which may be provided, for example, by painting that portion of the first area with a low-reflectivity paint. Thus, if the first area 28 is viewed from a direction indicated as 48, the low-reflectivity region 46 appears as a spherically concave ring with the light pipe 18 protruding through its center. The low-reflectivity region 46 may be as large or as small as necessary to produce a desired effective reflectivity for the first area 28. As mentioned above, a low reflectivity is preferred where the first area 28 is to be less reflective than the second area 30. Thus, the low-reflectivity region 46 may cover the entire first area 28, or may cover only a portion that is necessary to achieve a desired difference in effective reflectivity between the first area and the second area 30. The latter option will sometimes be desirable for reasons set forth in U.S. Pat. No. 4,052,615 Cho.

The second area 30 in the embodiments of FIGS. 1 and 2 is typically a mirrorlike surface, which may be too reflective when the first area 28 has a very low effective reflectivity. Accordingly, means for adjusting the effective reflectivity of the second area 30 are provided at 38. The reflectivity adjusting means 38 may be any conventional device—such as a variable beam attenuator or a variable neutral density filter—for varying the level of radiation which passes through a given plane.

Figure 3:
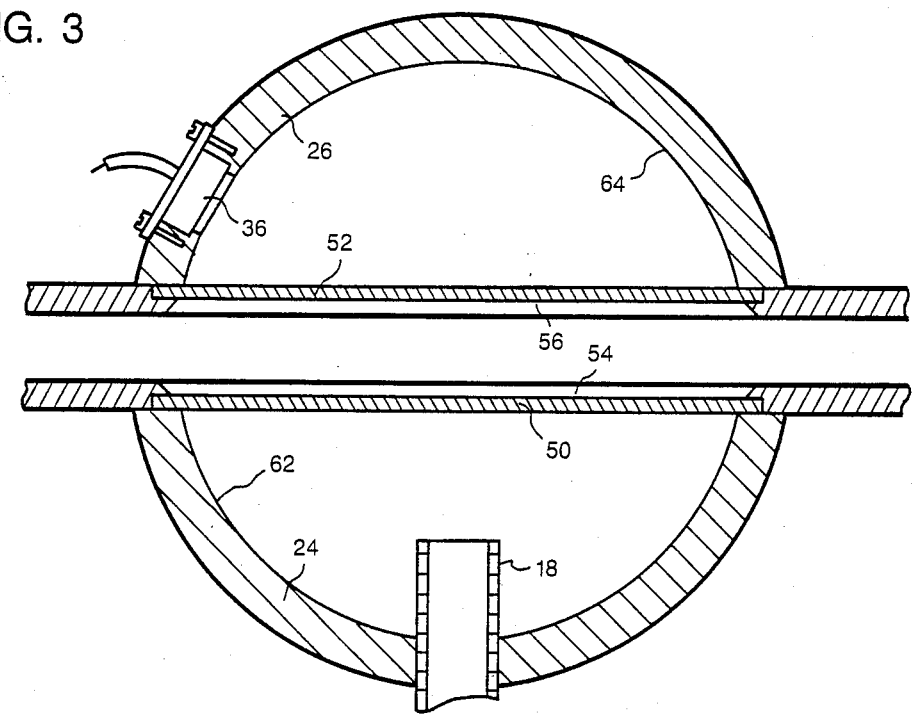
FIG. 3 is a generally schematic, partially sectional view of a further embodiment of the invention.
Figure 4:
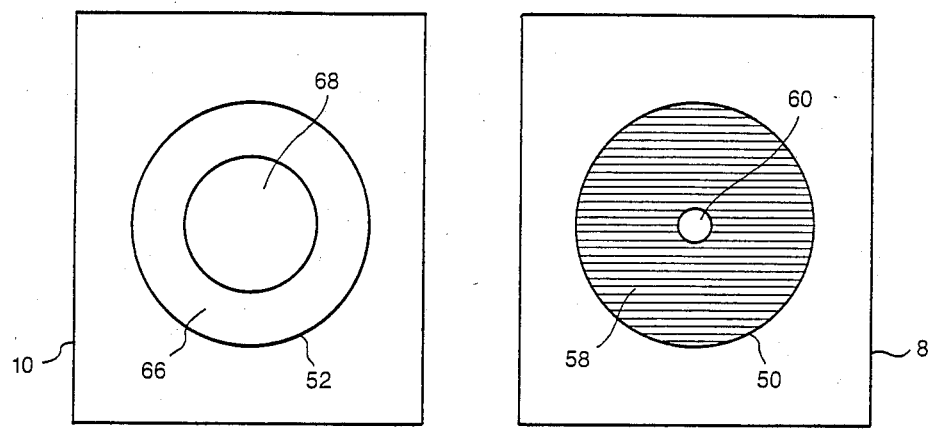
FIG. 4 is a plan view, somewhat schematic, of certain features of the embodiment of FIG. 3.

Alternative means for adjusting effective reflectivity are illustrated in FIGS. 3 and 4. In FIG. 2, two plates 50, 52, typically made of glass, are shown attached to the source unit 8 and detector unit 10, respectively. The usual function of these plates is to protect the mirrored, spherically concave inner surfaces 60, 62 (FIG. 3) of hemispherical bodies 24 and 26 (In FIGS. 1 and 2, these surfaces are the first and second areas 28, 30.). However, in the embodiment of FIG. 3, as further illustrated in FIG. 4, planar surfaces 54 and 56 further serve as the first area 28 and second area 30, respectively. A low effective reflectivity for the first area 28 may be provided by suitably painting either planar surface 54, or the opposite surface of plate 50, over a low-reflectivity region 46 of the first area. A center region 60 of the plate 50 is left transparent so that radiation coming from the light pipe 18 is free to impinge on the first surface 32.

The second area 30 includes a transparent region 66 and a circular high-reflectivity region 68 that may be formed by any conventional means for producing mirrorlike surfaces, as by vapor deposition of gold or aluminum. The effective reflectivity of the second area 30 may be varied by varying the diameter of the high-reflectivity region 68. This method is not particularly suited to on-line adjustment, since adjustment would be made, for example, by selecting one plate of a desired reflectivity from a series of plates of varying reflectivity and installing the plate in the detector unit 10. In the experimental design that has been tested, satisfactory measurement results were obtained on paper magazine stock having a nominal basis weight of 55 grams per square meter, where the center region 60 has a diameter of about ¾ inch, the first and second areas 28, 30 of the plates 50, 52 have diameters of about five inches, and the high-reflectivity region 68 has a diameter of about three inches. Alternatively, a relatively large high-reflectivity region 68 may be provided—still leaving a transparent region 66—and any conventional means 38 (FIG. 2) for adjusting effective reflectivity may be added to the embodiment of FIG. 3.

In the operation of the invention as embodied in FIG. 1, a radiation beam directed from the lamp 14 is modulated by the rotating chopper disc 16. The optical filters (not shown) separately mounted in the chopper disc 16 are sequentially passed through the radiation beam so that radiation transmissions through the filters and the light pipe 18 are time-multiplexed, thus enabling the use of a single detector 36. Radiation passing through the light pipe 18 impinges on the first surface 32 of the sheet 2. Portions of the radiation may be absorbed by, scattered by, or transmitted through the sheet 2. These interactions with the sheet 2 may occur many times, and radiation that leaves the sheet from either side may further interact with the first or second areas 28, 30. Radiation reflected from the first or second areas 28, 30 is redirected to the first surface 32 or second surface 34 of the sheet 2, and so on, until radiation is finally detected at 36. Since scattering will in general be a more dominant mode of interaction than transmission, the ultimately-produced moisture measurement can be made more sensitive to conditions prevailing near one surface of the sheet than to the other by adjusting the relative levels of radiation redirected from the first and second areas 28, 30 to the sheet 2. In the embodiment of FIG. 1, this is accomplished by providing a significantly greater effective reflectivity for the second area 30 than for the first area 28. Thus, FIG. 1 postulates the need to increase the sensitivity of the measurement to conditions prevailing near the second surface 34 of the sheet 2.

As stated, radiation is finally received by the detector 36, which sequentially produces responses, the magnitudes of which depend on the levels of radiation received. These responses are communicated via line 70 to a conventional ratio analyzer circuit 72, which produces a measurement response 74 indicative of the moisture content of the sheet 2.

FIG. 5 illustrates the process for which the previously-described apparatus are specifically designed. For ease of description, the thickness dimension of the sheet 2 is exaggerated in relation to other features of the drawing.

A moisture-altering operation 40 typically deposits moisture in selected cross-machine zones of the sheet 2, as indicated at 80, and thereby commences a period of substantial moisture stratification therein. During the period of substantial moisture stratification, a traversing infrared moisture sensor 6 (Enclosed by the dashed line) in accordance with this invention directs infrared radiation from a source unit 8 onto a first surface 32 of the sheet 2. The radiation undergoes multiple interactions with the sheet 2 and with first and second areas of the sensor 6. These areas have significantly different effective reflectivities, the effective reflectivity of the second area being significantly greater than that of the first area for the process illustrated in the drawing. One or more detectors within a detector unit 10 of the sensor 6 detect selected wavelengths of infrared radiation which has undergone multiple interaction. When the sheet material 2 is paper, the selected wavelengths will preferably include two sets, one set being of about $1.83\mu$ and $1.93\mu$, and the other being of about $1.89\mu$ and $2.12\mu$, thus incorporating the teaching of U.S. Pat. No. 4,577,104 Sturm. The detector or detectors produce detector responses that are communicated via line 70 to a ratio analyzer circuit 72, where they are processed as shown, for example, in U.S. Pat. Nos. 3,405,268 Brunton, or 4,577,104 Sturm, to produce a measurement response 74 that is communicated to a computer 76. The computer 76 controls performance of the moisture-altering operation 40, as indicated at 82, in response to the measurement response 74 and in accordance with a moisture target 78 set within the computer.

The illustrated embodiments show the first area 28 as less reflective than the second area 30. However, it should be understood that this is not a requirement unless the high-moisture stratum of the sheet is toward the detector unit 10 rather than the source unit 8. Where the high-moisture stratum is toward the source unit 8, the first area 28 will have a significantly greater effective reflectivity than the second area 30.

There is also no requirement that a single detector be used in a time-multiplexing arrangement as illustrated, since the invention can easily be used in a plural detector arrangement such as that illustrated, for example, in U.S. Pat. No. 3,405,268 Brunton.

Although the invention has been described in terms of preferred embodiments, the description is intended as illustrative rather than restrictive. Those skilled in the art to which the invention relates will recognize that numerous modifications may be made without departing from the spirit and scope of the invention.

What is claimed is:

1. Apparatus for measuring the moisture content of sheet material, such as paper, comprising:
   (a) a source unit having a first area adapted to generally face a first surface of the sheet, the first area having an effective reflectivity;
   (b) means, disposed within the source unit, for directing infrared radiation onto the first surface;
   (c) a detector unit having a second area adapted to generally face a second surface of the sheet, the second area having an effective reflectivity, and the detector unit being spaced apart from the source unit to form a pass gap of sufficient width to allow substantially free movement of the sheet therethrough; and
   (d) means, disposed within the detector unit, for detecting infrared radiation that has emitted from the directing means and repeatedly interacted with the sheet and the first and second areas, and for producing detector responses from which measurements of the moisture content of the sheet can be derived, wherein the effective reflectivity of the second area is significantly greater than the effective reflectivity of the first area, the apparatus thereby being adapted to yield greater measurement sensitivity to moisture conditions prevailing in the sheet near the second surface than to those conditions prevailing near the first surface.

2. Apparatus for measuring the moisture content of sheet material such as paper, comprising:
   (a) a source unit having a first area adapted to generally face a first surface of the sheet, the first area having an effective reflectivity;
   (b) means, disposed within the source unit, for directing infrared radiation onto the first surface;
   (c) a detector unit having a second area adapted to generally face a second surface of the sheet, the second area having an effective reflectivity, and the detector unit being spaced apart from the source unit to form a pass gap of sufficient width to allow substantially free movement of the sheet therethrough; and
   (d) means, disposed within the detector unit, for detecting infrared radiation that has emitted from the directing means and repeatedly interacted with the sheet and the first and second areas, and for producing detector responses from which measurements of the moisture content of the sheet can be derived, wherein the effective reflectivity of the first area is significantly greater than the effective reflectivity of the second area, the apparatus thereby being adapted to yield greater measurement sensitivity to moisture conditions prevailing in the sheet near the first surface than to those conditions prevailing near the second surface.

3. Apparatus as in claim 1 or claim 2 wherein the more reflective of the first and second areas is positioned on a side of the sheet corresponding to a high-moisture stratum thereof.

4. Apparatus as in claim 3 further comprising means for adjusting the effective reflectivity at least one of the first and second areas.

5. Apparatus as in claim 4 wherein the effective reflectivity of the less reflective of the first and second areas is constant.

6. Apparatus as in claim 3 wherein the more reflective of the first and second areas is planar.

7. Apparatus as in claim 3 wherein the more reflective of the first and second areas is spherically concave.

8. Apparatus as in claim 3 further comprising means for separately detecting infrared radiation comprising a first set of wavelengths of about $1.83\mu$ and $1.93\mu$, and a second set of wavelengths of about $1.89\mu$ and $2.12\mu$.

9. A process for measuring the moisture content of sheet material, whereby moisture measurements are made via a traversing infrared moisture sensor, comprising the steps of:
   (a) directing infrared radiation from a source unit of the sensor onto a first surface of the sheet material to initiate multiple interactions of the radiation with the sheet material, with a first area of the source unit which first area has an effective relectivity, and with a second area of a detector unit of the sensor which second area has an effective reflectivity differing significantly from the effective reflectivity of the first area; and
   (b) detecting, within the detector unit, selected wavelengths of the radiation to produce detector responses from which the measurements are derived.

10. A process as in claim 9 wherein the measurements are made during a period of substantial moisture stratification in the sheet material.

11. A process as in claim 9 wherein the more reflective of the first and second areas is positioned on a side of the sheet material corresponding to a high-moisture stratum thereof.

12. A process as in claim 9 further comprising the step of altering the moisture content in selected cross-machine zones of the sheet material.

13. A process as in claim 12 further comprising the step of controlling performance of the altering step in response to the measurements.

14. A process as in claim 9 wherein the selected wavelengths comprise two sets of wavelength, one set being of about $1.83\mu$ and $1.93\mu$, and another set being of about $1.89\mu$ and $2.12\mu$.

* * * * *